United States Patent [19]

Byler

[11] 4,214,588
[45] Jul. 29, 1980

[54] FOOT WARMING DEVICE

[75] Inventor: William H. Byler, Winter Park, Fla.

[73] Assignee: William H. Byler, Revocable Trust, Sarasota, Fla.; William H. Byler and Thelma T. Byler, Trustees

[21] Appl. No.: 897,248

[22] Filed: Apr. 18, 1978

[51] Int. Cl.² .............................................. A61F 7/00
[52] U.S. Cl. ..................................... 128/402; 128/403
[58] Field of Search ............................ 128/399–403, 128/258, 254, 382, 383; 150/2.1–2.6; 30/2.6

[56] References Cited

U.S. PATENT DOCUMENTS

| | | | |
|---|---|---|---|
| 267,435 | 11/1882 | Leiter | 128/402 |
| 518,579 | 4/1894 | Annenberg et al. | 36/2.6 |
| 647,294 | 4/1900 | Cropley | 150/2.5 |
| 670,878 | 3/1901 | Hogan et al. | 150/2.1 |
| 699,778 | 5/1902 | Upham | 150/2.5 |
| 912,527 | 2/1909 | Batter | 128/254 |
| 970,907 | 9/1910 | Forbes et al. | 128/402 |
| 2,397,232 | 3/1946 | Birnes et al. | 150/2.1 |
| 2,429,234 | 10/1947 | Miller | 128/379 |
| 2,675,630 | 4/1954 | Youmans | 36/2.6 |
| 3,075,517 | 1/1963 | Morehead | 128/24.1 |
| 3,092,112 | 6/1963 | Zelony | 128/403 |
| 3,830,676 | 8/1974 | Elkins | 128/403 |

FOREIGN PATENT DOCUMENTS

| | | | |
|---|---|---|---|
| 137766 | 1/1903 | Fed. Rep. of Germany | 128/258 |
| 295292 | 4/1932 | Italy | 36/2.6 |
| 124753 | 3/1928 | Switzerland | 36/2.6 |

Primary Examiner—Lawrence W. Trapp
Attorney, Agent, or Firm—Pennie & Edmonds

[57] ABSTRACT

A heat storage device having a tubular configuration suitably adapted to warm the feet of a user, including use, especially in bed, to induce sleep. In a preferred embodiment, the heat storage device contains water as the principal heat storage source, and the tubular configuration is flexible for convenient application to a user's feet. The heat storage device effectively supplies heat to both upper and lower portions of the feet while having means which easily adjust to foot size and for variation of heat capacity with ventilation in a simple, economical manner.

10 Claims, 6 Drawing Figures

FIG. 1.
FIG. 2.
FIG. 3.
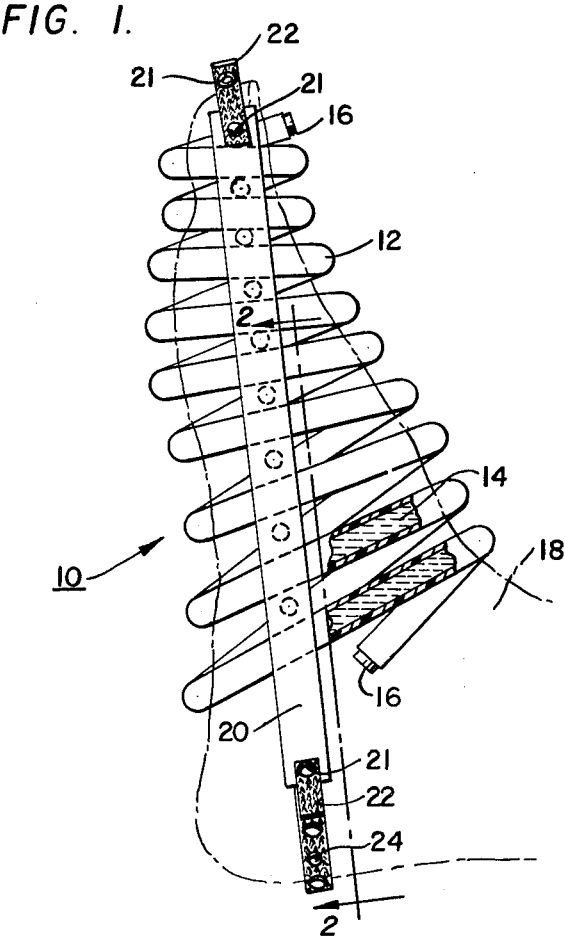
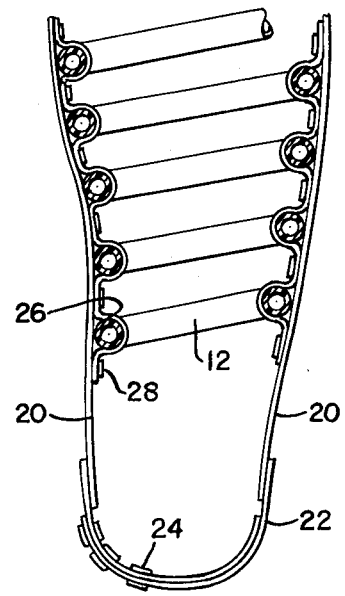
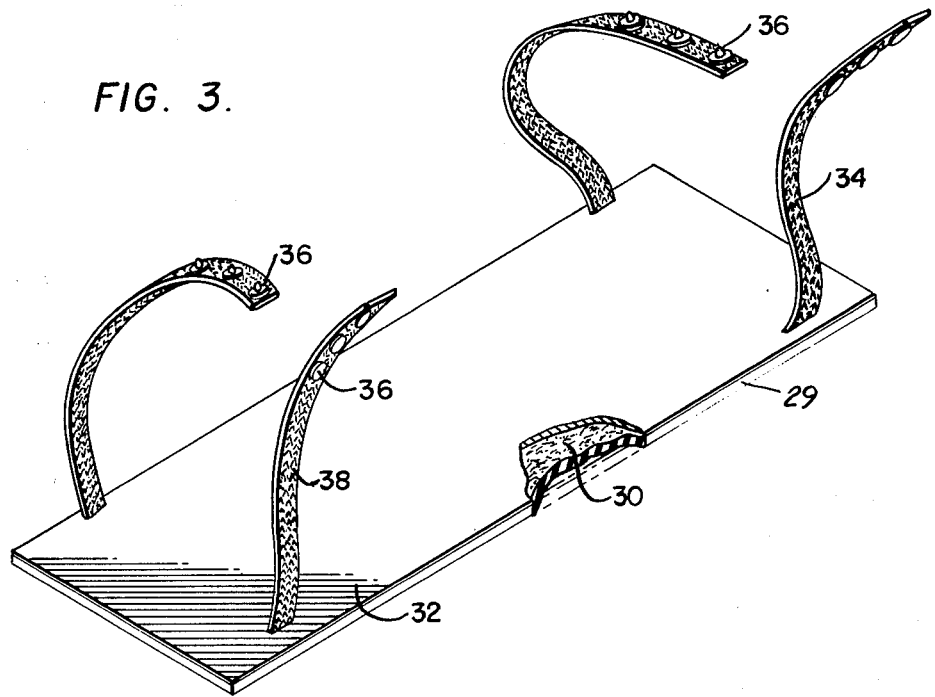

FOOT WARMING DEVICE

BACKGROUND OF THE INVENTION

1. Field of the Invention

The present invention discloses a heat storage type body warmer incorporating a tubular configuration with a contained heat source which provides heat to the feet of a user.

2. Description of the Prior Art

Numerous attempts have been made in the prior art to provide a solution for what is commonly referred to as "cold feet", a problem which is widespread and which is, perhaps, most troublesome when it causes delay of sleep. The most conventional solution for cold feet in bed has been use of heat sources such as a hot water bottle, hot iron, or hot brick. These attempts have achieved marginal success since frequently only one side of the foot is heated, there being no provision for heating both the upper and lower parts of the feet simultaneously, and freedom of movement is restricted.

Warm socks have also been used for heating feet, including socks having self-contained warming devices. These attempts have also achieved marginal success since the heat level is difficult to control with frequent over-heating due to lack of ventilation and this may result in disturbed sleep.

The patent art has also recognized attempts to provide a supply of heat to various parts of the body. For example, U.S. Pat. No. 3,830,676 discloses a heating pad through which heated liquid may be circulated. These flow-through devices are cumbersome and obviously are not suitable for use in bed. U.S. Pat. No. 2,429,234, on the other hand, teaches a device for conveying heat from the torso of the body to the extremities by mechanical means for forcing air as the heat transfer medium. This system is also cumbersome and has limited utility for heating feet. Another example of prior art body warming devices is that disclosed in U.S. Pat. No. 518,579, the device being used to conserve body heat by means of insulation. However, this device is not suitable for bed usage. Yet another example of a prior art device is that disclosed in U.S. Pat. No. 267,435 which includes a metal spiral through which fluids are permitted to flow. It is obvious that this device is totally uncomfortable and provides, at best, a marginal means for heating portions of the body.

It has now been found that by practice of the present invention numerous defects of the prior art have now been overcome by a foot warmer having means which adequately warm upper and lower parts of a foot simultaneously and in a convenient, comfortable fashion without requiring an overly complex combination of elements.

SUMMARY OF THE INVENTION

The invention, generally stated, provides a heat storage device having a tubular configuration suitably adapted to warm the feet of the user. In a preferred embodiment, the heat storage device includes means for delivering heat to upper as well as lower parts of the feet using flexible tubing and water as the principal heat storage sources and further means for simple adjustment of the heat storage capacity, the distribution of heat and ventilation.

It is an object of the present invention to provide one or more spirals of flexible tubing containing a material having relatively high specific heat capacity in a variable configuration for easy application to the contour of a user's foot, while providing flexible longitudinal supports.

It is also an object of this invention to provide a foot warming device having elastic means disposed for retaining the foot warming device about the foot of an individual which permits comfortable usage.

The principal categories of embodiments incorporate the following combination of elements:

1. One or more spirals of flexible tubing filled with water, the preferred material; flexible longitudinal supports through which the tubes are threaded so that spacing can be varied and adjustments can be made to fit the feet; elastic bands or similar simple means to hold the device on the feet; easily mounted separate sole piece for wear outside the bed if desired.
2. A longitudinal row of water-filled flexible tubing mounted on one or more support parts forming a sole piece; one or more bands of flexible metal or metal fabric, aluminum foil being preferred, in contact with the sole part, extending over the feet, adjustable to conform to the feet; elastic bands to hold the device on the feet.
3. A longitudinal row of tubes and sole piece the same as (2) above; one or more bands of water-filled flexible tubes extending over the upper parts of the feet adjustable to conform to the feet; elastic bands to hold the device on the feet.

It is an object of this invention to provide a foot warming device employing heat storage material having relatively high specific heat.

It is a further object of this invention to provide flexible tubing as a container for this heat storage material so arranged that the device can be worn comfortably in bed.

It is another object of this invention to provide simple means for adjustability of the device to conform to individual feet, to provide the needed ventilation, and to allow for variation of heat capacity.

It is a further object of this invention to provide means for supplying heat to the upper as well as the lower parts of the feet.

Other objects and features of the present invention will become more apparent from the following description taken in conjunction with the accompanying drawing.

BRIEF DESCRIPTION OF THE DRAWING

FIG. 1 is a diagrammatic view taken in partial side elevation of an embodiment of the present invention disposed about a user's foot;

FIG. 2 is a sectional view of the embodiment of FIG. 1 taken along section lines 2—2;

FIG. 3 is a perspective view illustrating a separate sole piece which may be used as a component of the foot warming device of the present invention, especially when worn out of bed;

DESCRIPTION OF THE PREFERRED EMBODIMENTS

Figure 4:
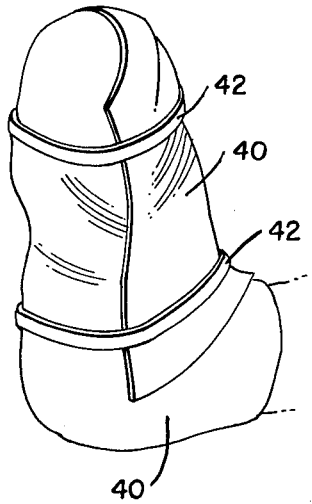
FIG. 4 is a perspective view illustrating a cover disposed about the foot warming device of the present invention.

FIG. 1 illustrates foot warming device 10 having a generally spirally disposed flexible elastic tubing 12 containing a fluid having relatively high specific heat capacity such as water 14, which may be contained by suitable means illustrated as a plug 16. The spirally disposed tubing 12 is positioned about the foot 18 of an individual and may be supported in position by two flexible support bands or strips 20 positioned along opposite sides of the foot 18. The ends of the strips are attached by conventional means such as rivets 21, to adjustable elastic members 22 having clasping elements 24 conveniently positioned as desired. The tubing used for the foot warming device of the present invention may be any elastic material available to the art and may be configurated of plastic or the like for comfort purposes. Although the tubing is illustrated as having a spiral configuration in FIG. 1, it will be appreciated by those skilled in the art that other patterns may be configurated as desired, as well as spacing of the loops. Thus, for example, instead of the helical configuration, it will be appreciated that the tubing may be raised in any desired configuration about the foot of the user and may be supported by suitable framing means or snap fasteners if desired for convenient adjusting means. Also, if desired, the device may be held comfortably by means of the tubing disposed about the heel portion of the foot.

FIG. 2 illustrates one convenient means for securing the tubing 12 to the two flexible support strips 20 using bands 26 of elastic materials so that adjustment of the lengths of the spiral tubing may be effected to permit comfortable fitting about the foot. The bands 26 may be attached to the flexible support strips by any convenient means such as illustrated rivet fasteners 28. These elastic bands may be individual pieces of elastic band material fastened to the side supports with snap fasteners or may be formed from continuous band material. This system allows variation of spacing of the spiral loops, of total length of tubing, and of size of tubing. Thus, the device provides simple adjustability of heat capacity and ventilation.

FIG. 3 represents a simple sole piece attachment which has obvious advantages whenever the device is worn out of bed. The sole piece attachment 29 may be only a piece of rubber or plastic 30 or this base may be covered by a heat reflecting layer 32 such as steel or aluminum foil. The back set of holding elastic bands 34 can be attached just back of the midpoint of the sole and snap fastened above the heel using snap-fasteners 36 at a position which ensures maintenance of position on the foot when walking. Forward holding elastic band 38 also having snap-fasteners 36 may be secured about the foot as desired.

FIG. 4 represents a form of overall heat insulating cover 40 which may be especially useful for conserving heat and promoting comfort when the device is worn out of bed. Openings for ventilation may be provided as desired. The cover 40 may be held in position by rubber band-like members 42, or the cover may be simply secured in position by means of tape, string or cord.

Figure 5:
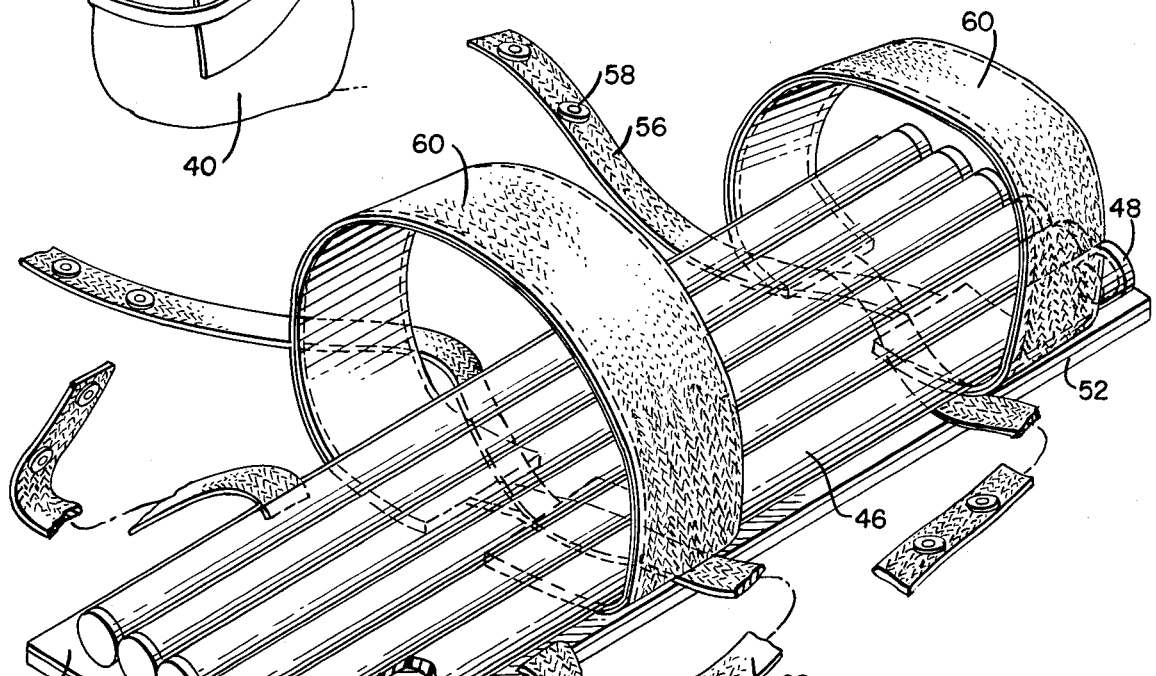
FIG. 5 is a perspective view illustrating another embodiment of the foot warming device of the present invention.

FIG. 5 illustrates an embodiment of foot warming device 44 having a plurality of parallel sections of tubing 46 which may be closed by plugs 48 to contain liquid 50 therein. Each section of tubing 46 is illustrated disposed on platform 52 which is similar to the sole piece attachment 29 and which may also have a surface layer of a heat reflective material 54. Securing bands 56 having snap fasteners 58 may be secured as desired to platform 52 to provide a means for retaining the foot warming device to the foot of a user. Bands 60 represent metal foil such as aluminum laminated to an insulating layer such as wool cloth or felt disposed to conduct heat from the tubes to upper parts of the foot. Elastic bands 56 and 62 with snap fasteners 58 and 64 provide means for adjusting the bands for snug fit thus enhancing heat transfer.

Figure 6:
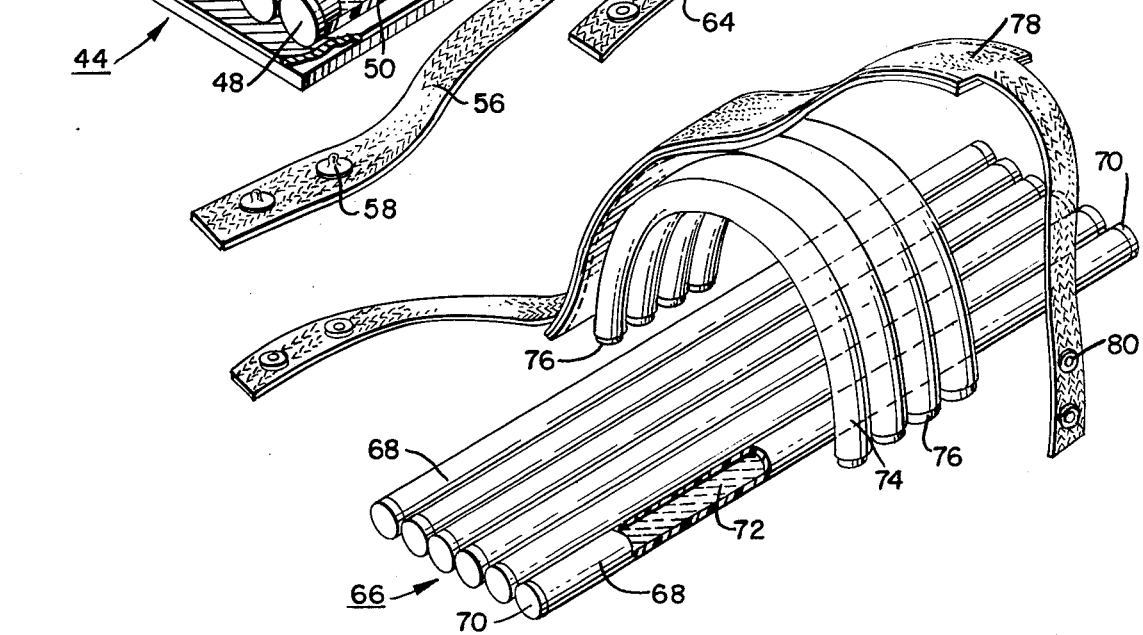
FIG. 6 illustrates a perspective view of yet another embodiment of the foot warming device of the present invention.

FIG. 6 illustrates another embodiment of the foot warming device 66 of the present invention. In addition to having parallely disposed sections of tubing 68 with plug members 70 disposed to contain liquids 72, the foot warming device further includes arcuate tubings 74 which conveniently supply heat about the foot of the user in addition to the heat provided to the sole portion by tubings 68. Arcuate sections of tubing 74 are similarly configurated with plug members 76 for containing a liquid heat source as desired. In order to retain the arcuate sections of tubing 74 and the horizontally disposed sections of tubing 68 about the foot of a user, felt band 78 may be conveniently secured about the arcuate sections of tubing and attached to the parallel disposed sections of tubing when in position by snap fastening members 80. Alternatively, elastic bands may be attached to the group of arcuate tubes and passed under the parallel disposed sections of tubing to provide simple adjustability of fit in similar manner to bands 56 and 62 of FIG. 5. Foot warming device 66 provides a convenient means for delivering heat to the upper parts of a foot while being comfortably retained in position.

Results of experimental work with latex tubing $\frac{1}{4}$, $\frac{3}{8}$ and $\frac{1}{2}$ inch I.D.; 1/16 and 3/32 inch wall thickness suggest a preference for the $\frac{3}{8}$ inch I.D. with 1/16 inch wall thickness. About 25% of the heat capacity of this size when filled with water is represented by the latex. Larger sizes tend to be less comfortable and less easily handled. A given length of water-filled $\frac{3}{8}$ inch tubing has about 2.4 times the heat capacity and provides about 2 times the heat capacity per unit cost and 1.3 times the heat capacity per unit weight compared to the $\frac{1}{4}$ inch size. Weight is a significant consideration in relation to comfort in bed.

Comparing the different design types, a major advantage of the spiral design is superior heat distribution. With a given tube size, the spiral design can have about double the heat capacity of the longitudinal tube design. For a man's size, the latter type can use only about 6 feet of $\frac{3}{8}$ inch tubing whereas the spiral type can use about 12 feet, although 8 feet seems to provide sufficient heat capacity and allows good space for ventilation. So the spiral design is more adjustable and has less weight per unit heat capacity because it has less fittings. Comparisons such as this versus a type employing gypsum slab as the heat storage element show the types of this invention to have substantial advantage. These tube types are not limited to water as principal heat storage element; for example, lithium fluoride and some common hydrates have lower specific heat capacity than water but higher than most materials and can be used in powder or granular form as means to avoid liquid.

The principal objective is to deliver to the feet in a comfortable temperature range, sufficient heat energy to induce sleep. In a series of experiments with the FIG. 5 longitudinal design incorporating six lengths of $\frac{3}{8}$ inch, 1/16 inch wall latex tubing (one foot length), with one 3 inch band of aluminum foil conductor effective heat was delivered over a period of about 25 minutes from a starting temperature of 130° F. (54.5° C.). The effective heat delivery time can be extended either by substituting water-filled tubes for the metal conductor or by using the spiral design (FIG. 1) which provides maximum heat storage. The larger heat storage capacity also allows the option of lowering the starting temperature for a given heat delivery. In fact, some people who have certain blood circulation problems are advised to avoid prolonged exposure to heat above the near normal body temperature range. On the other hand, they are advised to avoid chilling which causes reduced blood circulation. The present invention offers attractive means for these and other people with the cold feet problem to help themselves during waking hours as well as in bed. For example, two sets of these special slippers can be used so that one set is being charged with heat while the other set is in use. Experiments on supplying heat to these devices for charging show that a simple oven fitted with one or more 100-watt bulbs or heating elements is quite sufficient (can be homemade). Other heat sources such as the kitchen stove can be used. A temperature of about 145° F. (62.7° C.) is preferred but a range of about 95° F. (35° C.) to about 158° F. (70° C.) may be useful, the lower side being for those with certain blood circulation problems.

It will be apparent to those skilled in the art that numerous changes and variations may be made in the description of the present embodiments without departing from the essence of the present invention. Accordingly, it is intended that the description of the present invention and accompanying drawings are to be interpreted for purposes of illustration rather than as limiting the practice of the present invention.

What is claimed is:

1. A foot warming device which comprises, in combination, a plurality of lengths of a flexible elastic tubing adapted to contain a liquid having a high specific heat capacity, each length of tubing being substantially coextensive with and disposed in parallel relation to other lengths of tubing, means for supporting each length of tubing in a disposition for contacting a substantial surface of the foot to be warmed, elastic means connected to said supporting means adapted for removable securement of said tubing in said foot contacting position, and one or more flexible bands having high heat conductivity conformed about upper parts of the foot and secured in contact with the tubes by attached adjustable bands.

2. The foot warming device of claim 1 wherein said supporting means includes a platform having a wearing surface, said elastic means including at least a pair of elastic members extending from opposed sides of said platform and snap fastener means carried by each said elastic member for intercooperating, adjustable engagement thereby to removably mount said platform to said foot.

3. The foot warming device of claim 1 further comprising a plurality of arcuate sections of tubing arranged side-by-side, and elastic band means received around said arcuate sections of tubing and said lengths of tubing for positioning said sections of tubing at a location over the top of said foot to be warmed.

4. A foot warming device which comprises, in combination, at least one length of a flexible elastic tubing adapted to contain a liquid having a high specific heat capacity and disposed substantially as a spiral to provide a foot receiving opening whereby said foot is adapted to contact said tubing along the loops of said spiral upon receipt into said opening, means for supporting each length of tubing in a disposition for contacting a substantial surface of the foot to be warmed, said supporting means including flexible support strips, one of said support strips extending along one side of said spiral and another of said support strips extending along the opposite side of said spiral, a band for securing each loop of said spiral to a respective one of said support strips, and elastic means connected to said supporting means adapted for removable securement of said tubing in said foot contacting position.

5. The foot warming device of claim 4 wherein the tubing has a diameter of about ⅜ inch I.D., and the wall thickness of the tubing is about 1/16 inch.

6. The foot warming device of claim 4 including a plurality of lengths of said tubing, and wherein said each length of tubing is substantially coextensive with and disposed in parallel relation to other lengths of tubing.

7. The foot warming device of claim 4 wherein the combination further includes a platform, said platform having a wearing surface, and means for removably mounting said platform on said foot.

8. The foot warming device of claim 7 or 2 wherein said platform includes a surface formed of a heat reflective material opposite said wearing surface and adjacent said tubing.

9. The foot warming device of claim 4 wherein said elastic means includes elastic members connecting adjacent ends of said support strips.

10. The foot warming device of claim 9 wherein at least one pair of adjacent ends are connected by two elastic members, and further including snap fastener means carried by said two electric members for intercooperating, adjustable engagement thereby to adapt said foot warming device to a plurality of foot sizes.

* * * * *

UNITED STATES PATENT AND TRADEMARK OFFICE
CERTIFICATE OF CORRECTION

PATENT NO. : 4,214,588
DATED : July 29, 1980
INVENTOR(S) : William H. Byler

It is certified that error appears in the above-identified patent and that said Letters Patent are hereby corrected as shown below:

In the masthead of the patent, line [75] delete "Winter Park" and in its place include -- Sarasota --.

Signed and Sealed this

Fourth Day of November 1980

[SEAL]

Attest:

SIDNEY A. DIAMOND

Attesting Officer

Commissioner of Patents and Trademarks